United States Patent [19]

Robertson

[11] Patent Number: 5,020,084
[45] Date of Patent: May 28, 1991

[54] ORE ANALYSIS

[75] Inventor: Malcolm E. A. Robertson, Ottery St Mary, England

[73] Assignee: National Research Development Corporation, London, England

[21] Appl. No.: 334,973
[22] PCT Filed: Sep. 7, 1987
[86] PCT No.: PCT/GB87/00626
 § 371 Date: Mar. 10, 1989
 § 102(e) Date: Mar. 10, 1989
[87] PCT Pub. No.: WO88/02111
 PCT Pub. Date: Mar. 24, 1988

[30] Foreign Application Priority Data

Sep. 12, 1986 [GB] United Kingdom ................. 8621983

[51] Int. Cl.$^5$ ............................................. G21K 3/00
[52] U.S. Cl. ......................................... 378/46; 378/45; 378/156
[58] Field of Search ...................... 378/44–50, 378/140, 143–144, 156, 158

[56] References Cited

U.S. PATENT DOCUMENTS

| | | | |
|---|---|---|---|
| 3,102,952 | 9/1963 | Hendee et al. | 378/45 |
| 3,924,127 | 12/1975 | Cheret et al. | 378/185 |
| 3,984,679 | 10/1976 | Lublin et al. | 378/50 |
| 4,228,351 | 10/1980 | Snow et al. | 378/54 |
| 4,278,883 | 7/1981 | Hathaway et al. | 378/79 |
| 4,317,035 | 2/1982 | Cohen et al. | 378/45 |
| 4,393,512 | 7/1983 | Wang | 378/156 |
| 4,486,894 | 12/1984 | Page et al. | 378/46 |
| 4,577,338 | 3/1986 | Takahashi et al. | 378/48 |
| 4,597,095 | 6/1986 | Akpan | 378/144 |
| 4,670,895 | 6/1987 | Penato et al. | 378/144 |

FOREIGN PATENT DOCUMENTS

| | | |
|---|---|---|
| 0067514 | 12/1982 | European Pat. Off. . |
| WO80/01718 | 8/1980 | PCT Int'l Appl. . |
| 1016906 | 1/1966 | United Kingdom . |
| 1025091 | 4/1966 | United Kingdom . |
| 1183514 | 3/1970 | United Kingdom . |
| 1248738 | 10/1971 | United Kingdom . |

OTHER PUBLICATIONS

Translation of the Baxmann et al. article titled "Basic Principles of X-ray Fluoresence Analysis".
Translation of W. German OffenLegungsschrift 2,649,512 by Denbsky.
Rolf Woldseth, Ph.D., "All You Ever Wanted to Know About X-Ray Energy Spectrometry", Jun., 1973, pp. 2.52-2.55.

Primary Examiner—Carolyn E. Fields
Assistant Examiner—David P. Porta
Attorney, Agent, or Firm—Cushman, Darby & Cushman

[57] ABSTRACT

A method for the rapid and sensitive analysis of heavy metal ores, especially those of gold and uranium, uses high-engery X-ray fluorescence spectroscopy. The invention is of particular interest for the measurement of samples from gold or bodies which typically have concentrations up to 10 ppm by mass. Preferred features include the use of an X-ray tube as a source, the counting of emitted fluorescence photons in energy bands selected to correlate with the characteristic x-ray fluorescence emissions of elements of interest, the excitement of the ore sample by irradiation with high energy bremsstrahlung radiation filtered through tin, the exploitation of polarization in analysis for uranium, the interposition of a platinum-group metal filter between the sample and the detector, and the use of high-purity germanium detectors. Techniques are described for the detection and elimination of inaccuracies due to the presence of certain interfering metals and correction for variations in sample density. Apparatus for use in the method of the invention is also disclosed and claimed.

27 Claims, 9 Drawing Sheets

ORE ANALYSIS

This invention relates to a method and apparatus for the analysis of samples of materials in which a finely divided heavy metal is dispersed in a non-metallic matrix, especially mineral ores containing gold, uranium, lead or platinum, using the technique of X-ray fluorescence (XRF).

The expression "heavy metal" used herein means tungsten and metals of higher atomic number.

A "non-metallic matrix" means a matrix consisting predominantly of non-metallic elements of low atomic number and/or their compounds, such as silica, but may also contain metals which are not "heavy metals" as defined above, either in elemental or in combined form, such as iron or barium.

The phenomenon of energy-dispersive X-ray fluorescence (XRF) is well-known. A sample, for example, of a mineral ore, is bombarded by high-energy X-rays and the fluorescence spectrum is analysed by counting the rate of emission of photons over a range of photon energies.

Assay laboratories of gold mines have a daily chore of analysing large numbers of samples of gold ore; these include both exploration samples taken to locate the gold-bearing ore, and random samples of ore actually mined, for accounting purposes. The total number of samples to be analysed per day typically ranges from a few hundred to several thousand depending on the size of the mine. A high throughput of samples is therefore highly desirable, in the order of say one sample per hundred seconds, and the only practicable assay method which can achieve this is the traditional fire assay method. This method, however, is expensive in time, labour, capital and running costs, and less accurate than desirable. It is essentially a manual process requiring large quantities of electricity and other consumables and in a typical laboratory dealing with 1,000–2,000 samples per day it is difficult to keep track of individual samples.

The use of X-ray fluorescence techniques to analyse ores for heavy metals is known, and is described for example in U.S. Pat. No. 3,404,275 (Martinelli) UK Patent Patent Specification 1080346 (VEB Vacutronic), German Offenlegungschriften 2046606 and 2140794 (Siemens AG), U.S. Pat. No. 4,224,517 (Lubecki) and European Patent Application 0166914 (Kernforschungzentrum Karlsruhe GmbH). Most of these disclosures contemplate the use of the characteristic K-emission peaks of the elements of interest. Such fluorescent emission may be stimulated by various sources, principally X-ray tubes (as in UK Patent Specifications 1070337 (Laurila) and 1017595 (UKAEA), and German Offenlegungschriften 2054464) and radionucleides (as in U.S. Pat. No. 3,404,275). None of these disclosures however uses high energy X-radiation within the meaning of the present disclosure.

None of the above prior art discloses the particular technique of counting the emitted fluorescence photons in energy bands selected in relation to the K-emission bands of the elements under analysis according to the present invention.

The use of metallic filters to shape the radiation incident upon the sample under analysis is known, for example, from U.S. Pat. No. 3,404,275 where a cadmium filter is used, but not for the particular purpose relevant to the present invention; this U.S. Patent, for example, uses for exciting the sample not high-energy X-rays, but $\delta$-rays. Again, UK Patent 1070337 discloses the use of nickel or cobalt filters but in the context of analysis for lighter metals than those contemplated by the present invention.

It is especially significant that none of the prior art discloses the preferred method according to the invention of producing the stimulating radiation—that is the exploitation of the broad bremsstrahlung peaks, filtered through a suitable metallic filter to excite the characteristic K-emission peaks of the metals under analysis. The use of germanium detectors, both of high purity (European Patent Application 0166 914 and UK Patent 4224571) and silicon or lithium-drifted (Offenlegungsschriften 2046606 and 2054464) is known but not in the context of the particular energy profile of the fluorescence photons analysed according to the invention.

It will be noted that none of the extensive prior art mentioned above is specifically directed to the analysis of ores for gold.

X-ray fluorescence techniques have been employed to analyze gold ores but these generally use the gold L band which does not give the sensitivity required for measurement of the one part per million level of gold which is critical. Small samples effectively of a few grams are the maximum that can be used in these known machines. The sample must be ground to an extremely fine powder and a binding resin or glaze added.

On the other hand some of the prior disclosures mentioned above (e.g. U.S. Pat. No. 4,224,517) are specifically concerned with analysis for uranium, but do not disclose the particular use of filtered high-energy bremsstrahlung radiation from a high-energy X-ray source according to the invention.

Metallic ores when bombarded by high energy X-radiation (which for the purposes of this description means radiation of by energy greater than 80 keV) emit fluorescence photons which are grouped into characteristic peaks.

The K X-ray fluorescence emission spectrum of gold is characterised by two peaks known respectively as the gold $K\alpha_1$ and the gold $K\alpha_2$ peaks respectively at approximately 68.8 keV and 67.0 keV.

According to the invention we have discovered a method of rapidly analyzing the ores of gold and other heavy metals which gives significant advantages over the known fire assay and L X-ray fluorescence techniques mentioned above. We are able, using preferred embodiments of the invention, to detect a concentration of 1 ppm by mass of gold at a confidence level of 95% in a counting time of 100 seconds.

The invention is applicable not only to gold but also to other heavy elements such as uranium, platinum and lead.

According to the invention we provide a method for analyzing a sample of ore for at least one heavy metal comprising exciting the ore with high energy X-rays to produce a fluorescence emission spectrum and measuring the intensity of the K-emission bands of the said metal or metals in the spectrum, characterised in that:
  (a) The X-rays are produced by an X-ray tube.
  (b) That most of the high energy bremsstrahlung peak is eliminated by a metallic filter interposed between the source and the sample to give high energy bremsstrahlung radiation of 100 to 130 kev incident upon the sample and
  (c) The number of fluorescence photons emitted in each of a plurality of energy bands is counted and compared, the width and energy of the bands being chosen in relation to the K-emission peaks of the metal or metals in the sample.

The anode material generally preferred for use in the method according to the invention is tungsten but the use of other anode materials is within the scope of the invention.

The method of the invention is especially relevant to the analysis of powdered gold ores containing below 10,000 ppm of gold and of ores containing both gold and uranium. Typically, in gold mining applications, 90% of the ore samples will be of concentration up to 10 ppm gold by mass. (All ppm data in this description are by mass).

The metallic filter interposed between the source and the sample is preferably tin metal at least 4 mm thick.

As will be described in more detail below, it is a preferred feature of the invention to pass the fluorescence photons emitted by the sample through a heavy metal filter to reduce the bremsstrahlung energy peak and thereby to enhance the relative number of counts in the K-bands of the metals under analysis. This filter is preferably of iridium or platinum when the ore contains gold, and of osmium when the ore contains platinum.

A preferred feature of the method according to the invention is that the photons emitted by the sample are counted by at least one detector of high purity germanium, preferably in the form of a disc of active thickness 2–4 mm.

In a preferred method according to the invention photons are counted in each of two background energy bands lying either side of the $K\alpha_1$ peak and in each of two signal energy bands lying between the background bands either side of the peak maximum and the total counts of photons in the background bands and in the signal bands compared, the two background bands being substantially equal in energy width and the two signal bands also being substantially equal in energy width.

This "symmetry" of the energy bands counted is an important preferred feature of the invention. The bands are chosen so as to show symmetry about the $K\alpha_1$ peak maximum, the object being to reduce errors due to shifts in the incident energy peak due to external causes such as supply voltage variations and temperature sensitivity of components. It is advantageous to compress the width of the signal bands and increase that of the background bands thus achieving a better signal:background count ratio. This "compression" of the peak is achieved by better detector resolution which in turn results from improvement in the physical configuration of the detector and its following electronics, reduction of noise and the like.

A further preferred method according to the invention uses not four but six energy bands. Using this method, as will be more particularly described hereinafter, it is possible to detect and eliminate interference from certain metals present in the heavy metal ore, for example thorium, mercury and tungsten.

In one such preferred method, applicable to the analysis for gold of ore samples containing mercury and/or tungsten, photons are counted in each of six adjacent energy bands embracing respectively:

(1) the gold $K\alpha_2$ peak on both sides of the maximum
(2) the trough between the gold $K\alpha_2$ and gold $K\alpha_1$ peaks
(3) the slope of the gold $K\alpha_1$ peak below its maximum
(4) the slope of the gold $K\alpha_1$ peak above its maximum
(5) the trough between the gold $K\alpha_1$ peak and the mercury $K\alpha_1$ peak
(6) the mercury $K\alpha_1$ peak on both sides of the maximum In another such preferred method, applicable to the analysis for uranium and gold of ore samples containing thorium, photons are counted in each of six adjacent energy bands embracing respectively:

(1) the region immediately below band (2) described below
(2) the thorium $K\beta_2$ peak
(3) the uranium $K\beta_1$ peak
(4) the uranium $K\beta_3$ peak
(5) the trough between the uranium $K\beta_2$ and $K\beta_{1+3}$ peaks
(6) the uranium $K\beta_2$ peak An important preferred method according to the invention for the analysis of gold in an ore is characterised in that:

(a) The X-rays are produced by an X-ray tube with a plutonium or uranium anode or secondary target.
(b) The ore sample is excited with the characteristic K X-rays of the material of the anode or secondary target and
(c) The fluorescence photons emitted by the sample are passed through an iridium filter.

According to the invention, a particular method of analysing a sample of ore, especially a gold ore or an ore containing gold and uranium, comprises: (1) Exciting the sample with high-energy bremsstrahlung X-rays having their maximum energy at about 115 keV produced by an X-ray tube with a tungsten anode and filtration through a metallic tin filter (2) Passing the X-ray fluorescence spectrum emitted by the sample at right angles to the exciting rays through a metallic iridium or platinum filter
(3) Detecting the fluorescence photons by a germanium detector
(4) Measuring the intensity of the $K\alpha_1$ emission bands of the gold content of the sample.

The invention further provides an apparatus for analysing the heavy metal content of an ore comprising:

(1) A source of high-energy X-rays
(2) Means to hold a sample of ore in the path of the X-rays
(3) Detector means to count the fluorescence photons emitted by the sample and characterised by
(4) Means to compare the counts of emitted photons in selected energy bands.

Characterised in that the X-ray source is a tube and a metallic filter is interposed between the source and the sample which eliminates part of the high-energy bremsstrahlung peak whereby high energy bremsstrahlung radiation of 100–130 keV is incident upon the sample.

In the apparatus according to the invention, the anode is preferably of tungsten and the filter of tin metal; the filter is perferably of tin 4–5 mm thick. Preferably, the apparatus also comprises a heavy metal filter interposed between the sample and the detecting means, preferably of osmium, iridium or platinum. Preferably the detector means is at least one body of high purity germanium, especially a plurality of high purity germanium discs each 2–4 mm thick. Also in the apparatus according to the invention, the fluorescence spectrum is preferably viewed at a scattering angle of from 80–100 degrees to the exciting radiation.

In an important preferred emodiment of the apparatus according to the invention, the X-ray source is a tube with a plutonium or uranium anode or secondary target and an iridium filter is interposed between the sample and the detecting means.

A preferred form of the apparatus according to the invention, associated with the preferred method set forth above, comprises means to count the emitted fluorescence photons in each of two background energy bands lying either side of the $K\alpha_1$ peak of the heavy metal under analysis and in each of two signal energy bands lying between the background bands and either side of the said $K\alpha_1$ peak maximum and to compare the total counts of photons in the background bands with the total counts of photons in the signal bands, the two background bands being substantially equal in energy width and the two signal bands also being substantially equal in signal width.

A particular aspect of the apparatus according to the invention is an apparatus for analyzing the gold and/or uranium content of a sample of ore by X-ray fluorescence, comprising an X-ray tube with a tungsten anode, a metallic tin filter, means to hold and retain the sample in the path of the X-rays emitted from the source and passed through the filter, an X-ray detector and means to detect the emission of photons of various energies from the sample, characterised by the interposition of a metallic platinum or iridium filter between the sample and the detectors and the use of germanium detectors. An iridium filter is preferred.

It is an important feature of the invention that the fluorescence radiation emitted by the sample is viewed at a scattering angle of about 90° to the exciting radiation. However, the scattering angle in any application is a matter of compromise between conflicting requirements as described below and the invention is not limited to any particular scattering angle. Generally it is found that an angle within the range 80°-100° is suitable. For purely mechanical considerations, an angle of exactly 90° is easiest to work with. However, the angle must also be chosen to minimise scattered non-parallel rays which give rise to background counts and from this point of view is preferably set at the Compton scattering minimum angle. Further, there is a correlation between peak energies and scattering angle—generally a particular peak shifts to a lower energy with an increase in scattering angle. A compromise between these three factors must be reached and it is generally found for the applications described herein that best results are obtained at a scattering angle of about 100°.

The X-ray tube may be any known type that produces high energy X-rays (i.e. photons) of the appropriate energy (as to which, see below) and is preferably water-cooled in a closed circuit cooling system with an integral radiator or chiller. In this description the expression "high energy" is used to indicate an exciting energy of 80 keV or more; the energy region 80–160 keV being of principal interest.

However, a preferred method of producing high energy X-rays for use in the method according to the invention uses an X-ray tube with a tungsten anode. Such tubes emit, in addition to the tungsten characteristic peaks, the highest of which lies at 69 keV and is too low to be of practical value in analysis for gold (the K-edge of which lies at 80.7 keV), a bremsstrahlung peak at 65 keV the upper edge of which lies at about 130 keV. The bremsstrahlung peak is generated by the slowing down of electrons in the tube anode. In this preferred method the tungsten characteristic peaks and most of the bremsstrahlung peak are eliminated by a metallic filter interposed between the source and the sample to give high energy bremsstrahlung radiation of 100–130 keV, preferably with a maximum at about 115 keV, incident upon the sample. This is in the form of a semi-Gaussian peak.

The metallic filter is preferably of tin metal and at least 4 mm, generally from 4–5 mm, thick.

The excitation voltage for the X-ray tube is optimised at about 130 kV when a 4 mm tin filter is used. The optimal voltage decreases as the tin thickness is increased, for example 125 kV with 5 mm tin.

The effective incident photon energy can be varied by altering the excitation voltage on the X-ray tube and the thickness of tin filter in front of it. Thicker filtration will both harden the energy (i.e. increase the average energy) and narrow the bremsstrahlung peak, but of course reduces the number of photons striking the sample. As the average energy moves downwards towards the K-edge of gold at 80.7 keV, the probability of exciting the gold will increase. However, in practice the resulting increase in signal will be partially counteracted from a signal to noise point of view by an increase in background and attenuation effects. Most of the peak is in the energy range 100–130 keV but the low energy tail does extend lower than this and, after single or multiple scattering by the sample contributes significantly to the background counts in the gold energy measurement region.

There are a number of practical limitations which restrict the ranges of excitation voltages and tin filter thicknesses one can use.

(a) With falling excitation voltage and increasing filter thickness the photon flux falls. We can compensate up to a point by reducing the distance between the X-ray tube anode and the sample, and between the sample and the detectors, but this introduces a number of other problems.

(b) It is advisable to restrict the effective photon energy to above 100 keV to minimise particle size effects.

(c) Simultaneous measurement of gold and uranium content requires a significant number of incident photons to be of higher energy than 115.6 keV, the K-edge of uranium.

The invention is not however limited to the use of highly filtered bremsstrahlung radiation as described above. It is also possible to achieve greater sensitivity by the use of an X-ray tube with uranium or (preferably) plutonium anode or secondary target, to generate uranium or plutonium characteristic K X-rays as well as bremsstrahlung. In this instance the characteristic radiation of the anode or secondary target material used to excite the sample and the bremsstrahlung radiation has its maximum at 150 keV, well above the energy region of interest. Some filtration of the bremsstrahlung radiation is still required, however, for example by the use of a tin filter as described above, to attenuate substantially the bremsstrahlung "tail" below 80 keV relative to the characteristic K-bands.

The secondary target may be internal or external; it will be appreciated that the use of a secondary external target has advantages when tubes with anodes of these metals are unavailable.

The lowest energy plutonium K X-ray, the $K\alpha_2$, is at 99.2 keV. Being characteristic radiation, this is monoenergetic, and there is no low energy tail, as with bremsstrahlung radiation. Similarly, the lowest energy uranium K X-ray is 94.6 keV as compared with the gold K absorbtion edge at 80.7 keV.

The relative attenuation of the low energy tail significantly reduces the background counts in the gold measurement and allows detection of lower gold levels. Another advantage is that the scattered characteristic radiation would be attenuated better by an iridium filter than the present bremsstrahlung, which would result in a higher sensitivity.

Plutonium K X-rays will excite both gold and uranium, whereas uranium K X-rays will excite only gold. This is one reason for preferring plutonium. A second reason is that the plutonium K X-rays are several keV higher in energy and, when scattered from the sample, will not contribute so much to the background counts in the gold energy measurement region.

The operating voltage of the uranium or plutonium anode X-ray tube is ideally higher than the tungsten anode tube, possibly as high as 300 kV or thereabouts. The higher the voltage, the higher the efficiency of production of characteristic radiation from the anode material. Also, the higher the energy of the bremsstrahlung, which is produced at the same time. As stated above some tin filtration is still needed to reduce the low energy tail of the bremsstrahlung but the latter should be a much lower fraction of the total exciting intensity.

An alternative to an X-ray tube using electrons for production of characteristic K X-rays of plutonium or uranium, is to bombard the target material with protons or alpha-particles. These produce much less bremsstrahlung when they are slowed down in the target material.

The ore samples must be finely ground but the average grain size, which should preferably be less than 100 microns, is not critical, although it has been found that with larger gold grain sizes in the ore better results are obtained by fine grinding. With fine gold grain sizes the sample may be ground to sub-millimetric size only. The sample is preferably contained in a cylindrical thin-walled container of plastic material such as acetal plastic, certain features of which are, as more particularly described below, preferred according to the invention.

A preferred feature of the invention is the use of a heavy metal filter interposed between the fluorescent sample and the detectors. For gold analysis using X-rays from a tungsten anode tube the heavy metal is preferably platinum or iridium; for platinum analysis an osmium filter is preferred. As will be more particularly described later with reference to the drawings, the use of a filter of one of these metals reduces the scattered bremsstrahlung peak at about 100 keV and enables the characteristic bands to be more readily detected by allowing the detection of higher count rates in the energy region of interest.

Apart from considerations of cost, a platinum filter should be used where the content of lead in the sample is to be measured, as the iridium $K\beta$ band overlaps the lead $K\alpha$ band.

The invention is not, however, restricted to the use of a filter of iridium or platinum, or indeed of any metal. As described herein, these particular metals are especially useful in analysis for gold and certain other elements using particular sources of exciting radiation. For example, platinum may be detected and analysed using an osmium filter. However, it is possible using other sources (for example radioisotopes) to analyse for low concentrations within the range contemplated by the invention and this is of particular relevance for the detection and analysis of lighter elements such as silver and copper as well as for that of gold, using the same detectors as are contemplated herein; such methods are, however, not within the scope of the present invention. A heavy metal filter cannot be used for the simultaneous measurement of light and heavy elements in similar dilutions. Nevertheless, whatever the excitation source, the use of an appropriate filter such as those described herein will generally make possible analysis at lower concentrations than is possible without such filter.

The above principles may be summarised by the statement that the filter medium is chosen to reduce the bremsstrahlung peak so as to enhance the count rate in the energy region of interest.

The invention is not limited to the use of filters consisting of a foil or sheet of the metal in question. For example, the filter may be made from finely divided metal dispersed in an epoxy or other resin matrix. Similar considerations also apply to the tin or other metal filter which, as mentioned above, is to be interposed between the radiation source and the sample.

The fluorescence photons passing through the iridium or platinum filter are preferably counted by at least one detector consisting substantially of metallic germanium. It is found that circular germanium detectors arranged in a regular array and orientated axially to the incident radiation are preferable. The combined use of germanium detectors and an iridium filter in preferred embodiments of the invention is an important feature which gives the capacity to detect gold in ore samples down to a concentration of 1 ppm at a confidence level of 95% in a counting time of 100 seconds.

The detector unit is preferably cooled to cryogenic temperatures by liquid nitrogen from a small cryostat automatically topped up from a large cryostatic reservoir.

The bombardment of the detectors by the high energy fluorescence photons emitted from the sample passing through an iridium filter generates a signal the intensity of which is amplified by pre-amplifiers (generally, one for each detector) and processed to give only the readings for the metals to be analysed.

The invention includes the analysis of sample containing other heavy elements such as uranium, platinum and lead. Indeed these elements are commonly found in gold ores. It is possible using the invention to measure two or more of these metals simultaneously, for example, especially uranium and gold. In principle it is possible to adapt the apparatus and method according to the invention to detect and analyze for elements in the periodic table down to, say, tungsten.

A method and apparatus corresponding to those of the invention may be used for measuring heavy metals such as gold in materials other than mineral ores; of especial importance is the measurement of gold in carbon from carbon-in-pulp plants.

The drawings illustrate the underlying physic and the layout of an apparatus according to preferred embodiments of the invention.

Figure 7A:
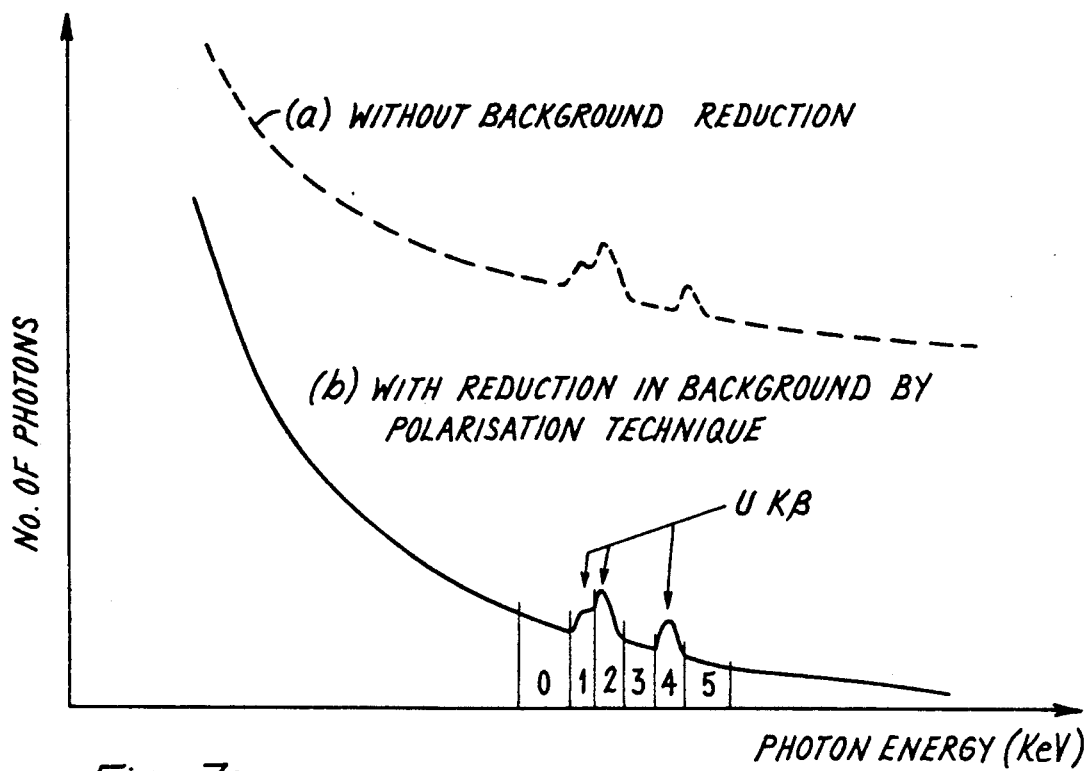
FIG. 7(a) represents, also on a greatly enlarged scale, the energy region of interest for uranium analysis.
Figure 7B:
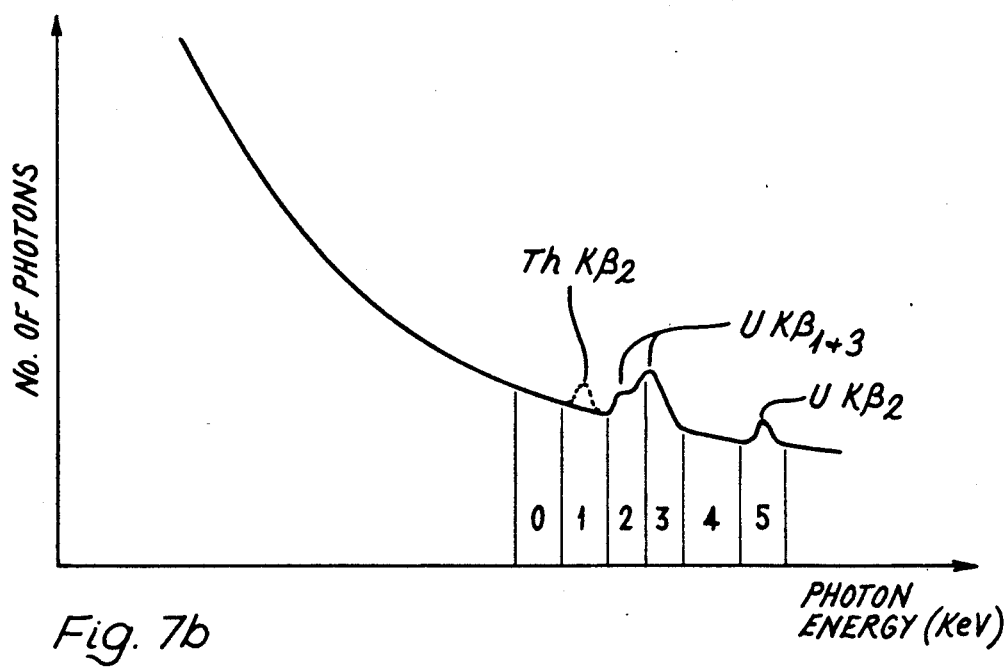
FIG. 7(b) shows, in a format corresponding to that of FIG. 7(a), the inter-relationship of thorium and uranium peaks.
Figure 7C:
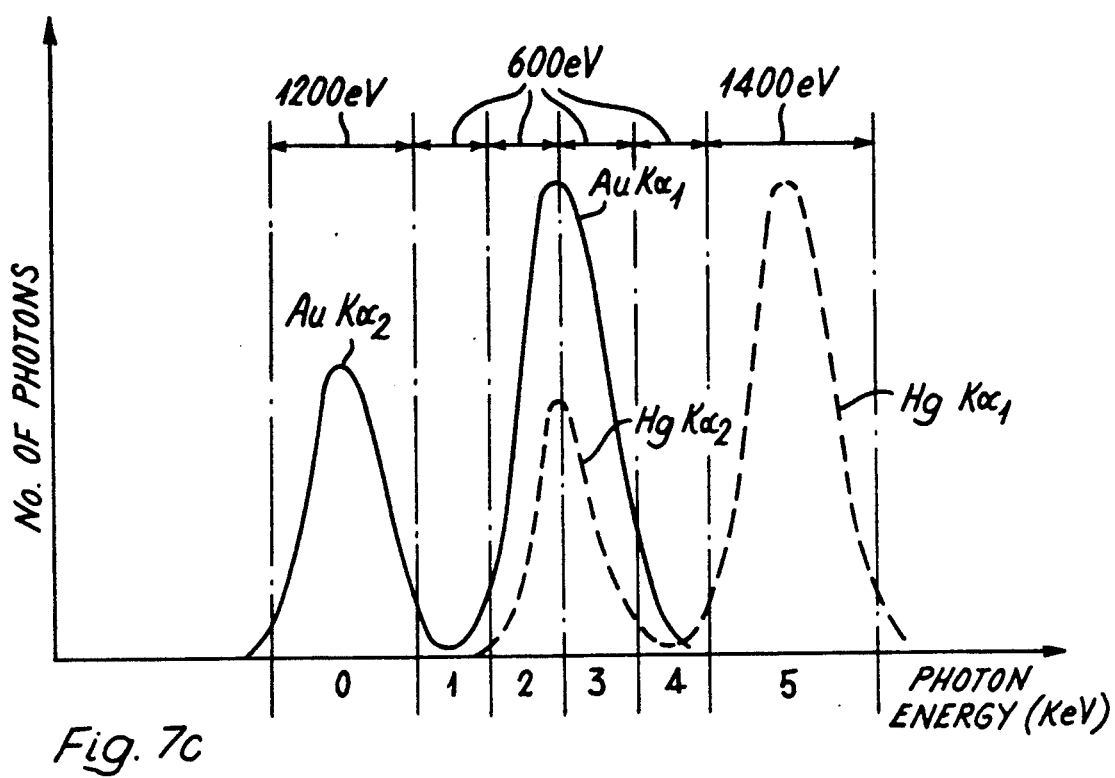

FIGS. 7(c) and (d) show the allocation of counting channels for, respectively, mercury and tungsten detection.

Figure 8:
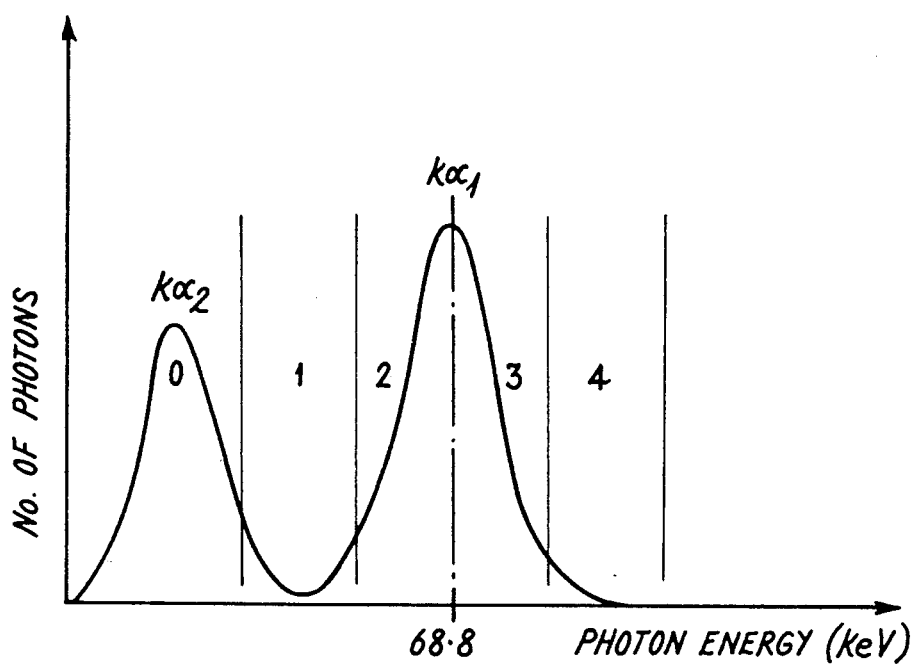

FIG. 8 represents the spectrum obtained with a solid gold check source.

Figure 9:
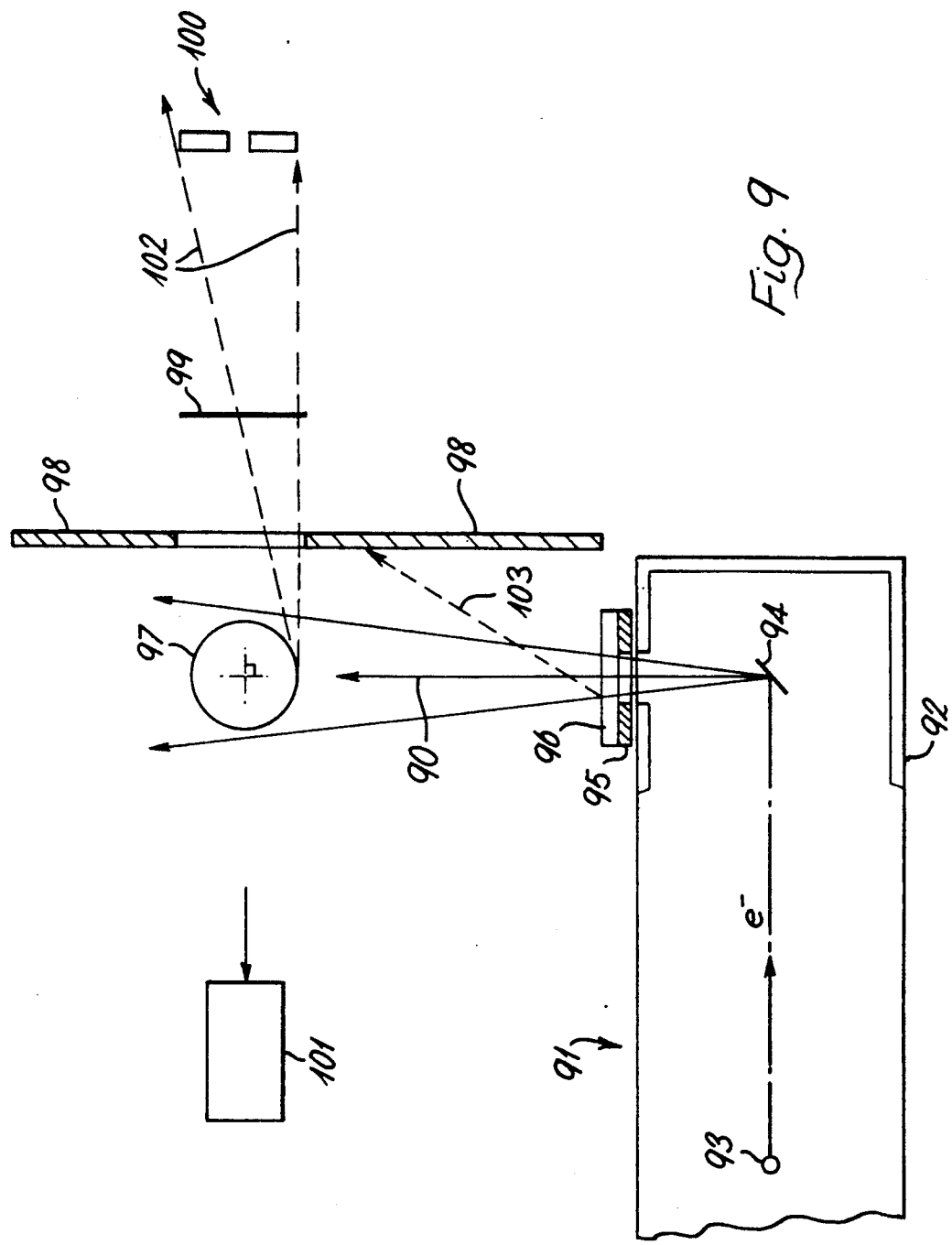

FIG. 9 is a schematic diagram showing the preferred geometry of the apparatus according to the invention.

Figure 10:
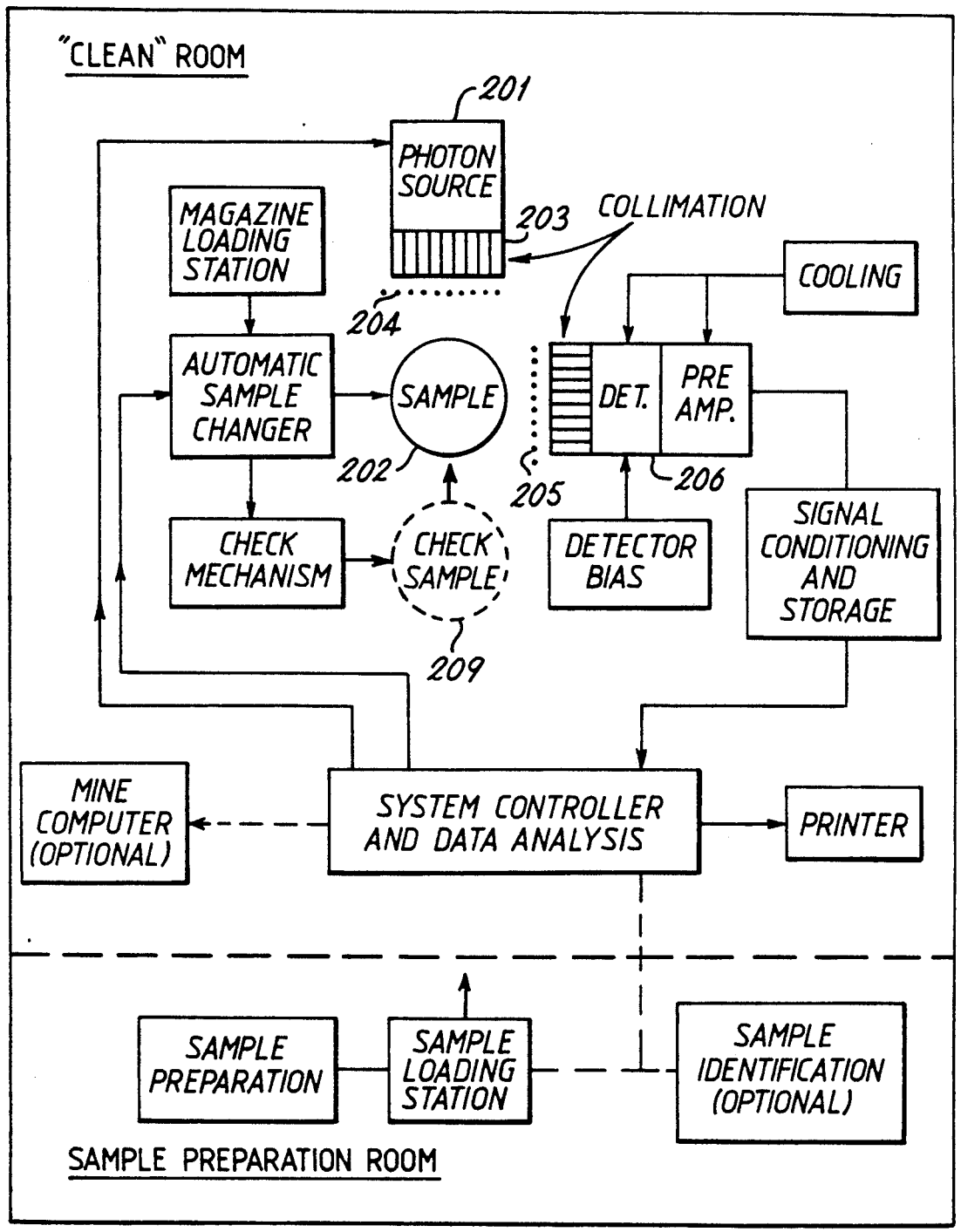

FIG. 10 is a block diagram illustrating a preferred embodiment of the apparatus according to the invention.

Figure 1B:
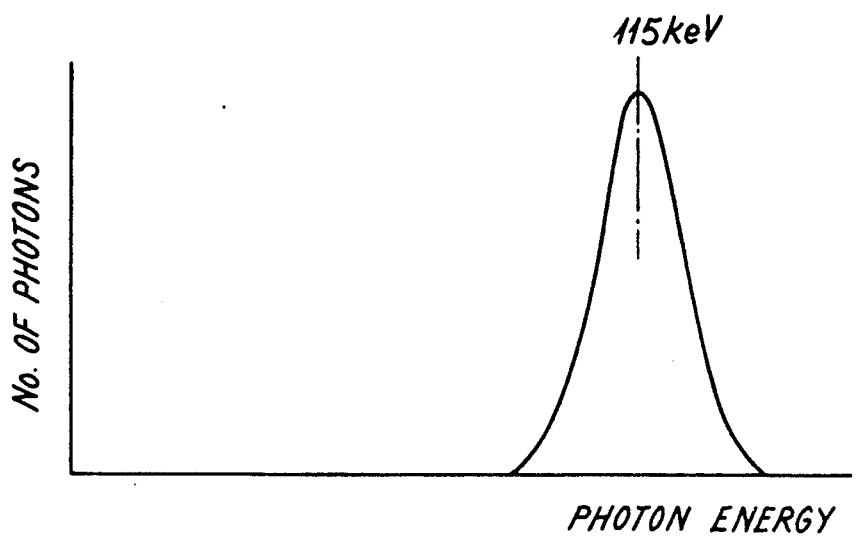
FIG. 1b shows the Gaussian distribution of high energy X-rays incident on the sample after passing through a tin filter of thickness greater than 4 mm.
Figure 1A:
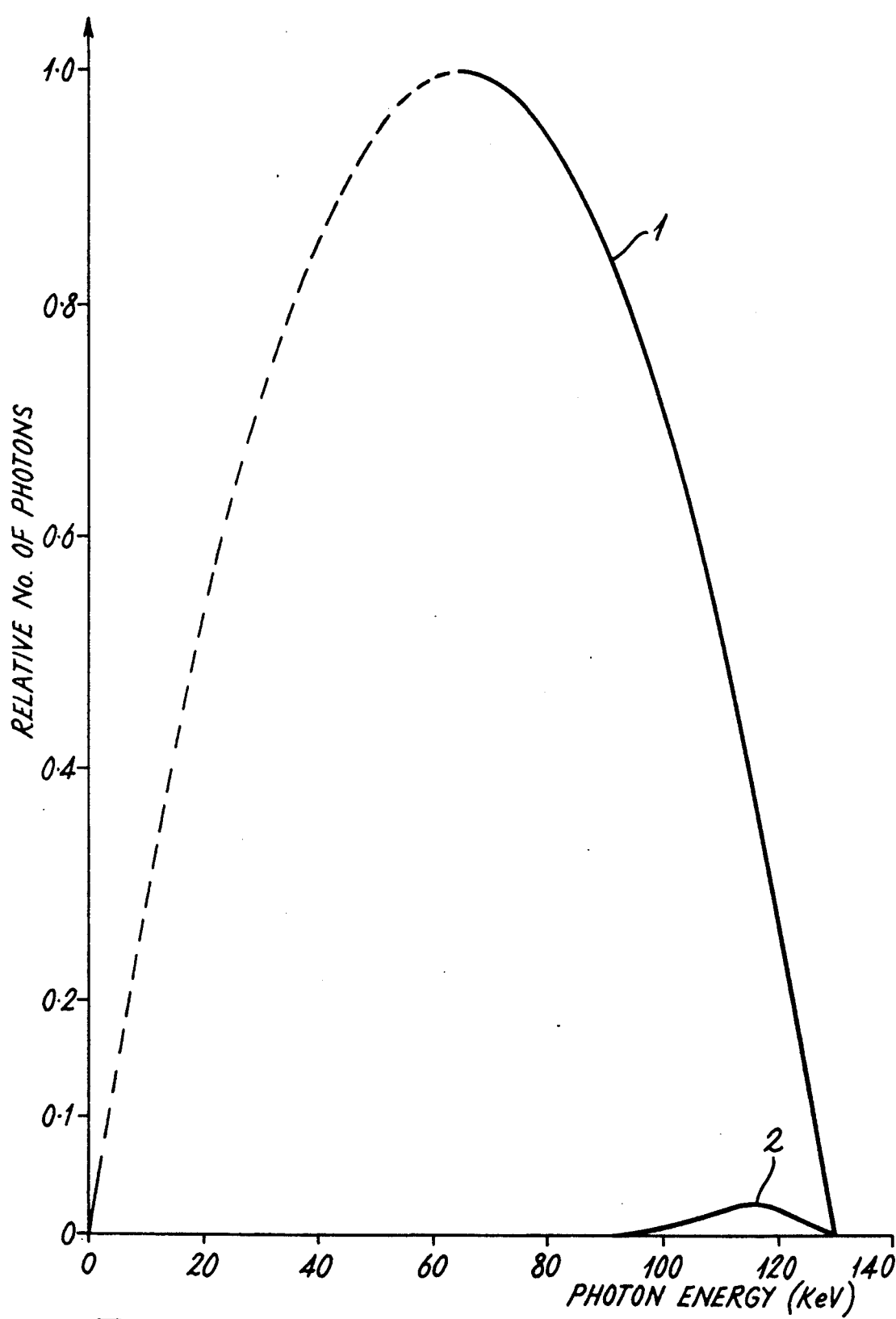
FIG. 1a shows a high-energy bremsstrahlung peak before and after shaping by filtration.

In FIGS. 1a and 1b the vertical axis represents the count of photons and the horizontal axis the energy of the exciting X-rays; this illustrates the spectrum of the X-rays bombarding the sample in the method and apparatus according to the invention. FIG. 1a shows, at 1, the broad bremsstrahlung peak emitted by an X-ray tube with a tungsten anode operated at 130 kV. It will be seen that there is a broad maximum at photon energy about 65 keV. According to the invention this broad maximum is reduced by filtration through metallic tin to give a reduced maximum for irradiation of the sample. This reduced maximum is shown on a larger scale in FIG. 1b, from which it will be seen that there is a peak at 115 keV with a Gaussian fall-off in number of counts on either side. A typical ore containing gold, lead and uranium, after bombardment with incident X-rays having the spectrum shown in FIG. 1b, emits at 90° fluorescence radiation having the spectrum illustrated in FIG. 2 in which the axes represent the same parameters. This Figure illustrates the characteristic peaks of gold, lead and uranium, those of particular significance for the invention being the gold $K\alpha_1$ peak at 68.8 keV and the gold $K\alpha_2$ peak at 67.0 keV. The maximum of the overall bremsstrahlung peak is shifted from about 115 to about 100 keV.

Figure 2:
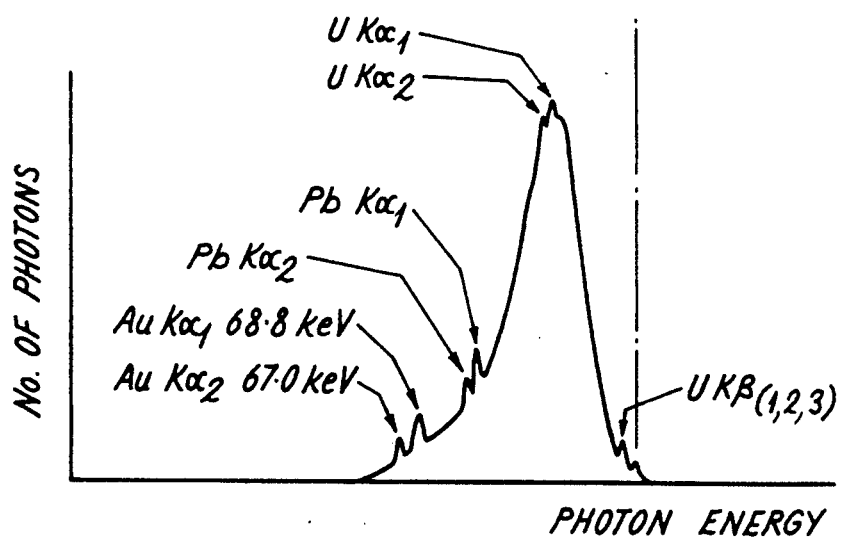
FIG. 2 shows the spectrum of high energy photons after scattering through 90° from a fluorescent sample containing gold, lead and uranium.

At the concentrations with which the invention is primarily concerned, (i.e. up to 10 ppm of ore) the gold peaks in the spectrum shown in FIG. 2 cannot be measured accurately with a time span convenient for industrial application by even the most sensitive means presently known. The maximum count-rate which each detector and associated electronics channel can handle is an inherently limiting factor. With known pulse-shaping techniques, as are envisaged for use in the invention, there is a trade-off between count-rate and detector resolution. At the detector resolution required for the analysis of the ores and other materials in which we are interested, the maximum input counting-rate is about 150,000 counts per second.

In the context of analysis for gold and uranium, however, only the fairly narrow energy bands around the gold $K\alpha$ (and uranium $K\beta$) peaks are of interest. An ideal detector would respond only to these. Unfortunately the detector response (illustrated diagrammatically in FIG. 5, see below) can only be partially optimized by careful selection of the detector thickness (in the range of 2-4 mm) and the photons in the large bremsstrahlung peak, which are of no interest, use up a large proportion of the detector live time.

Figure 3:
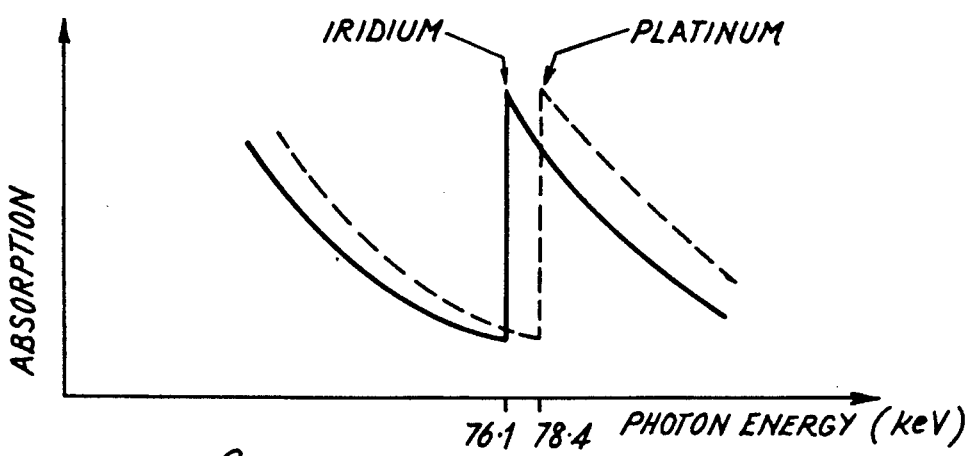
FIG. 3 represents the absorbtion spectra of iridium and platinum filters.

This difficulty is overcome according to the invention by the use of an iridium or platinum filter, the characteristic absorbtion spectra of which are illustrated in FIG. 3 in which the vertical axis represents absorbtion and the horizontal axis the energy of the incident radiation. When X-rays emitted by fluorescence from a sample in the apparatus according to the invention are passed through such a filter before detection the absorbtion spectrum of the filter is effectively superimposed upon the peak shown in FIG. 2 with result that the gold $K\alpha_1$ and $K\alpha_2$ peaks are much more readily detectable for the same total detector count rate, because there are more counts in the energy region of interest and statistical errors are reduced.

In other words, the iridium and platinum filters used according to the invention preferentially attenuate the higher energy radiations in which we are not interested. For example, a 0.125 mm thick iridium filter will transmit about 40% of the photons in the regions of interest (i.e. channels 0-5 in FIG. 6), but will transmit only about 20% of photons in the range 80-120 keV (the bremsstrahlung peak). As this latter peak comprises most of the photons, when we use the iridium filter we require about 5 times more power from the X-ray source to get the count-rate back to the maximum which the detectors can handle. However, the use of an iridium (for example) filter converts the spectrum shown in FIG. 2 to that shown in FIG. 4, and the proportion of photons in the region of interest, relative to the total count-rate, has increased by a factor of $0.4 \times 5$ i.e. doubled. Thus the use of the iridium filter has the same effect as doubling the number of detectors, and the statistical error in the result is reduced by about 2. A thicker filter would give more improvement.

Figure 4:
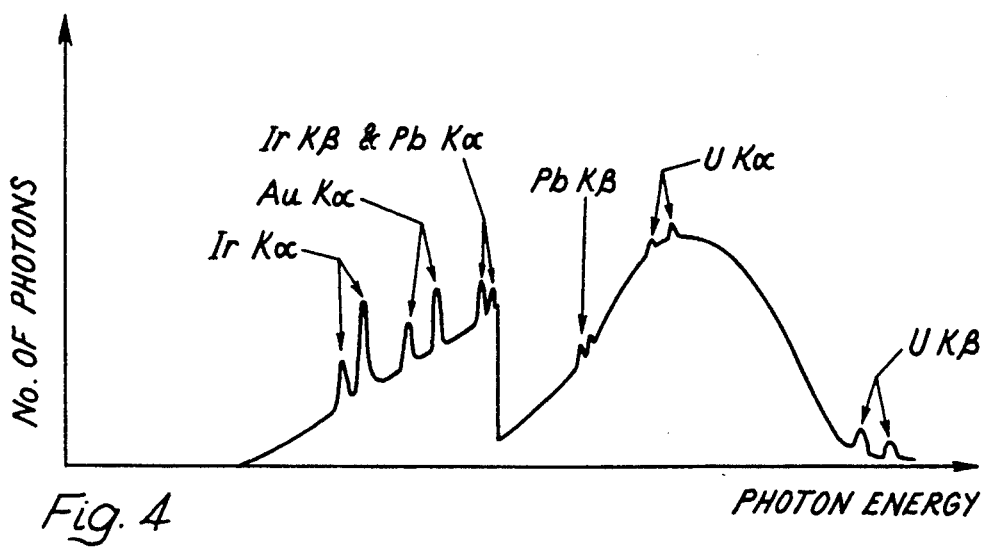
FIG. 4 represents the spectrum obtained by passing the scattered X-rays illustrated in FIG. 2 through a metallic iridium or platinum filter.
Figure 5:
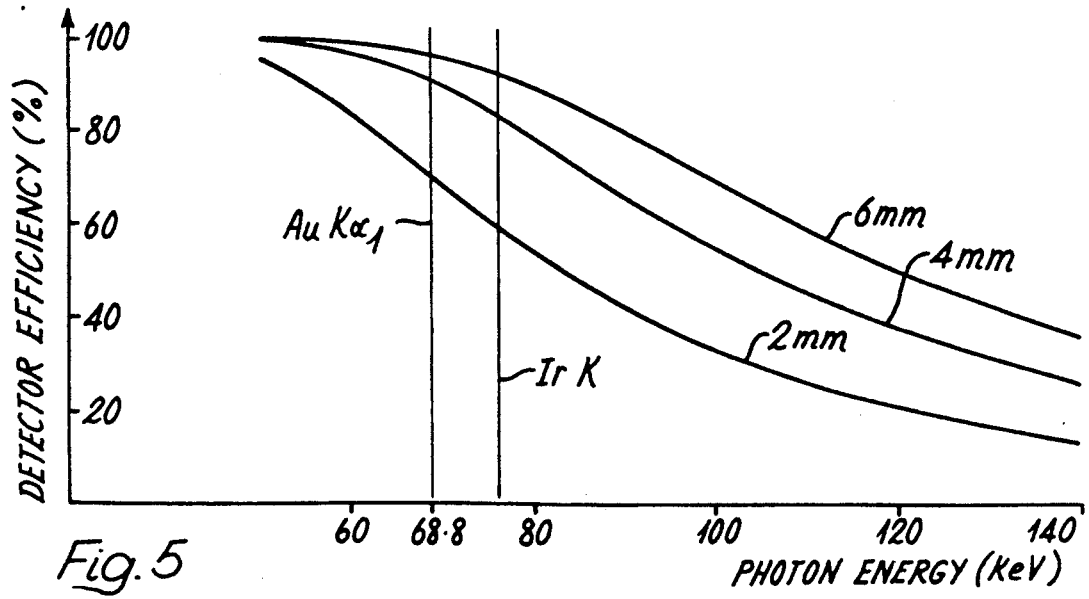
FIG. 5 represents the detector efficiency of germanium detectors of various thickness as used according to the invention.

This selectivity is enhanced according to the invention by the use of germanium detectors, the efficiency curve of which is illustrated in FIG. 5 in which detection efficiency (%) assuming photoelectric cross-section only is plotted against excitation energy (keV) for various detector active thicknesses. The efficiency falls assymptotically away from 100% with increasing exciting energy, being about 90% for a 4 mm thick detector at the crucial energy of 68.8 keV (the energy of the gold $K\alpha_1$ band). With increasing energy the efficiency falls off more rapidly to about 50% at 110 keV. It will be seen that a thickness of 2-4 mm gives a curve corresponding most closely to that of FIG. 4, and a detector thickness within this range is therefore preferred according to the invention for use in gold analysis.

Figure 6:
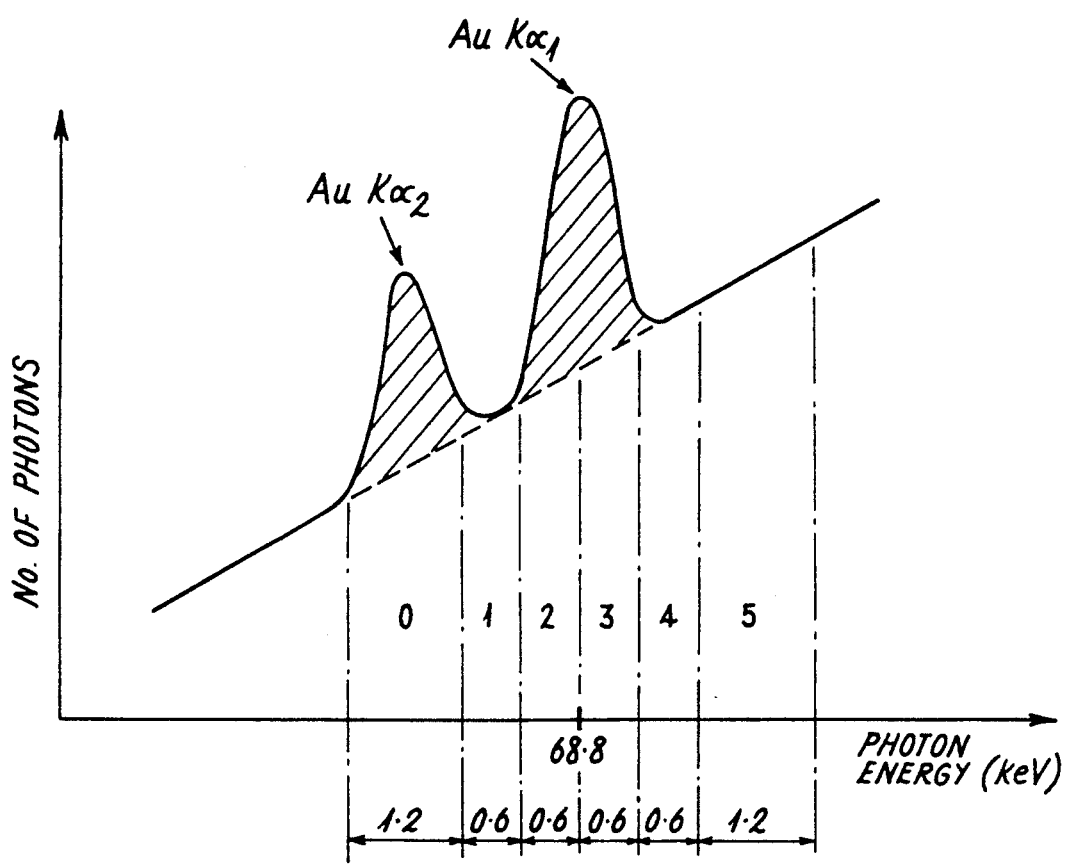
FIG. 6 represents, on a greatly enlarged scale, the gold $K\alpha_1$ and gold $K\alpha_2$ peaks used according to the preferred embodiments of the invention for the detection of gold in ore.

The spectrum resulting from the combined use of an iridium filter and germanium detectors in the apparatus according to the invention gives a spectrum as shown in FIG. 6 which corresponds generally to FIG. 4 but shows the gold $K\alpha_1$ and $K\alpha_2$ bands on a greatly enlarged scale. The associated electronic instrumentation is programmed in known manner to measure the number of impacts in selected band widths (or channels) such as those shown in FIG. 6. The instrumentation is programmed to compare the total signal plus background from the bands numbered 2 and 3 with the total background signal from the bands 1 and 4. The measurement of the gold content of the ore is therefore based not on an absolute measurement but on comparative measurements, thus eliminating uncertainties and inaccuracies inherent in the measurement of absolute values (e.g. the variations in excitation voltage or current in the X-ray source).

For gold measurement, bands 1-4 are used. Each band has a nominal width of 600 eV, but in practice these widths may be altered to suit detector resolution, for example bands 1 and 4 may be 500 eV wide, and bands 2 and 3 may be 700 eV wide, or vice versa. Bands 0 and 5 are used for diagnostic purposes.

The symmetry of the curve around the $K\alpha_1$ peak is important. In a diagnostic routine, a solid gold check source is used to determine the proportion of gold counts falling into each of channels 1-4. The spectrum from a solid gold source does not contain much scattered radiation (which originates predominantly from low atomic number material) and is shown in FIG. 8. The count in channel 2 is compared with the count in channel 3, and if these are unequal by more than a predetermined amount, the mid-point position between channels 2 and 3 is altered electronically, until symmetry is restored. Thus the fraction X of counts in channels (2+3) over channels (1+2+3+4) is measured and stored, and this indicates what fraction of the signal representing the gold $K\alpha_1$ band, which is nominally in channels 2 and 3, is spilling over into channels 1 and 4.

As will be mentioned in more detail below, the use of a check source of the metal being analysed is an important technique in practising the invention. When a series of samples are being analysed, as will normally happen, the check source is interposed between samples at intervals of, say, 4 or 5 samples, to determine and correct for any instrument drift due for example to temperature changes.

This process for gold is given by the algorithm:

$$G = \frac{S\left(\frac{T1}{T2} - k\right)}{x - y\left(\frac{T1}{T2}\right)}$$

where G = gold concentration in suitable units (e.g. g/tonne)
S = a normalized sensitivity factor (corrected for sample density and predetermined with calibration samples as described in more detail below)
K = a background factor (predetermined and corrected for sample density with calibration samples)
$T_1$ = counts in channels (2+3)
$T_2$ = counts in channels (1+4)
X = fraction of total signal counts in channels (2+3) (predetermined)
Y = fraction of total signal counts in channels (1+4)
(The total number of signal counts being the numbers in channels (1+2+3+4), so that Y = (1−X))
Ideally, with no spillover of gold signal into channels 1 and 4, X = 1 and Y = 0, and $$G = S\left(\frac{T1}{T2} - k\right)$$

The preferred normalizing technique according to the invention for the factor S is as follows. The counts from the sample depend both on the sample density and on the number of photons exciting the sample.

Variations due to the latter (e.g. due to changes in the X-ray generator current and high voltage) can be minimised by reference to the counts (H) obtained recently from a standard scatterer, which can be a solid gold check source or an aluminium background standard. The assumption is made that the instrument has remained stable since the last reading of the standard, which is reasonable. Thus, the variation in counts from the sample can be normalised to a standard excitation intensity, and the remaining variations are due to sample density alone, which is corrected for as described below.

It is within the scope of the invention to use a separate detector or detectors to check dynamically the excitation intensity and so remove the remaining uncertainty due to the time delay.

It has been found that, as sample density increases, the counts B in the background channels (corrected for overlap of signal) also increase, due both to more primary scattering and to more multiple scattering. The increase is partially offset by more attenuation and absorption. At the same time the signal counts per ppm also increase, due to the increased number of interactions, but not so fast as B. It has been determined, with a high correlation coefficient, that this process can be described by the equation:

$$S = M\left(\frac{B}{H}\right)N$$

where M and N are constants determined by regression analysis from a set of values of S and B obtained from known high value ore samples, having a range of densities. Even single samples can be prepared with a range of densities, by a combination of compression and grinding to different grain sizes. B should ideally be corrected for system deadtime, but in most practical cases the latter is largely compensated for in the actual measurement of M and N for similar photon energy spectrums. Variable lead peaks can cause a slight error, as they vary system deadtime.

The ratio T1/T2 in the gold equation given above is independent of system deadtime.

Other techniques for refining the density correction will readily be apparent, for example by consideration of higher energy sections of the photon energy spectrum which are less affected by multiple scattering. However, a particular advantage of basing the density correction on background channels on both sides of the signal channels is that primary attenuation and absorption effects are matched for both signal and background.

The values of M and N determined also compensate for counts due to the sample container itself, and other scattered radiation not originating from the sample.

The software can be made slightly easier by redefining the signal counts simply as those appearing in channels (2+3), in which case X=1. Then the equation becomes:

$$G = S \frac{\left(\frac{T1}{T2} - K\right)}{1 - y\left(\frac{T1}{T2}\right)}$$

This is not different, but the same process in slightly different format.

FIG. 9 illustrates schematically the geometry of excitation and detection according to the invention. As mentioned above, an important feature of the invention is that it provides a geometry for the apparatus which exploits the polarization of X-rays emitted from a source with a thick target. In FIG. 9, the X-ray source is indicated generally at 91 and comprises an X-ray tube 92, with tungsten cathode at 93 and tungsten anode at 94. The exciting radiation 90 from the anode 94 emerges through a lead collimator 95 and a tin filter 96 to strike a sample 97. Scattered and fluorescent radiation 102 from the sample emitted at about 90° to the incident exciting radiation passes through an aperture in a tin collimator 98 and an iridium or platinum filter 99 to the germanium detector array 100. This array may consist for example of two vertical rows of 8 detectors each. These are preferably circular and may for example be about 8 mm in diameter and about 2-4 mm thick. The tolerance in thickness is about 15% owing to limitations in the reproducibility of the lithium-diffused contact. Square cross-sectioned detectors would be preferable but currently available detectors are not suitable at high-count rates due to insufficient field strength in the rear corners resulting in low-energy tailing. A second filter and detector array (similar to that already described) may be provided at 101. Radiation 103 scattered from the tin filter 96 is stopped by the collimator 98.

The preferred use according to the invention of a scattering angle of about 90° is of especial significance for the measurement of uranium because the X-rays emitted from a thick target are often partially polarized. It is therefore important that, as shown in FIG. 9, the sample should be positioned so as to intercept X-rays emerging frOm the tube at 90° to the electron beam passing from cathode 93 to anode 94 in the tube.

This polarization phenomenon can, according to a preferred feature of the invention, be applied advantageously to the simultaneous analysis of gold and uranium. This is illustrated in FIG. 7(a), in which, as in previous figures, number of photon impacts is plotted vertically and photon energy in keV horizontally. The curve illustrated is that containing the uranium K bands on the high-energy side of the energy peak in FIG. 4. Broken curve (a) in FIG. 7(a) illustrates the curve obtained without the advantage of the reduction of background radiation obtained using the polarization technique described above. Curve (b) is obtained using the polarization technique, and illustrates the reduction in background counts. The channels 0-5 illustrated in FIG. 7 are counted and compared in a manner generally similar to that described above with reference to FIG. 6. In FIG. 7(a), the signal channels are channels 1, 2 and 4 and the background channels 0, 3 and 5. The edge of the uranium K-band is at 115.6 keV, thus if we are operating at 125-130 keV, reasonable excitation and polarization effects are obtained.

This technique for measuring uranium could suffer from interference by a thorium peak which occurs in channel 0 as shown in FIG. 7(a). In FIG. 7(b) is illustrated a method according to the invention of reducing or eliminating this interference. In FIG. 7(b) the channel numbers and energies have been shifted to lower energies and part of channel 0 re-allocated to provide an additional channel for thorium. The principal uranium $K\beta_1$ and $K\beta_3$ peaks then appearin channels (2+3) and the background measurement is determined from channels (0+4). The thorium $K\beta_2$ peak appears in channel 1. This not only reduces or eliminates thorium interference where uranium is being determined but also provides a method of determining thorium concentration.

Figure 7D:
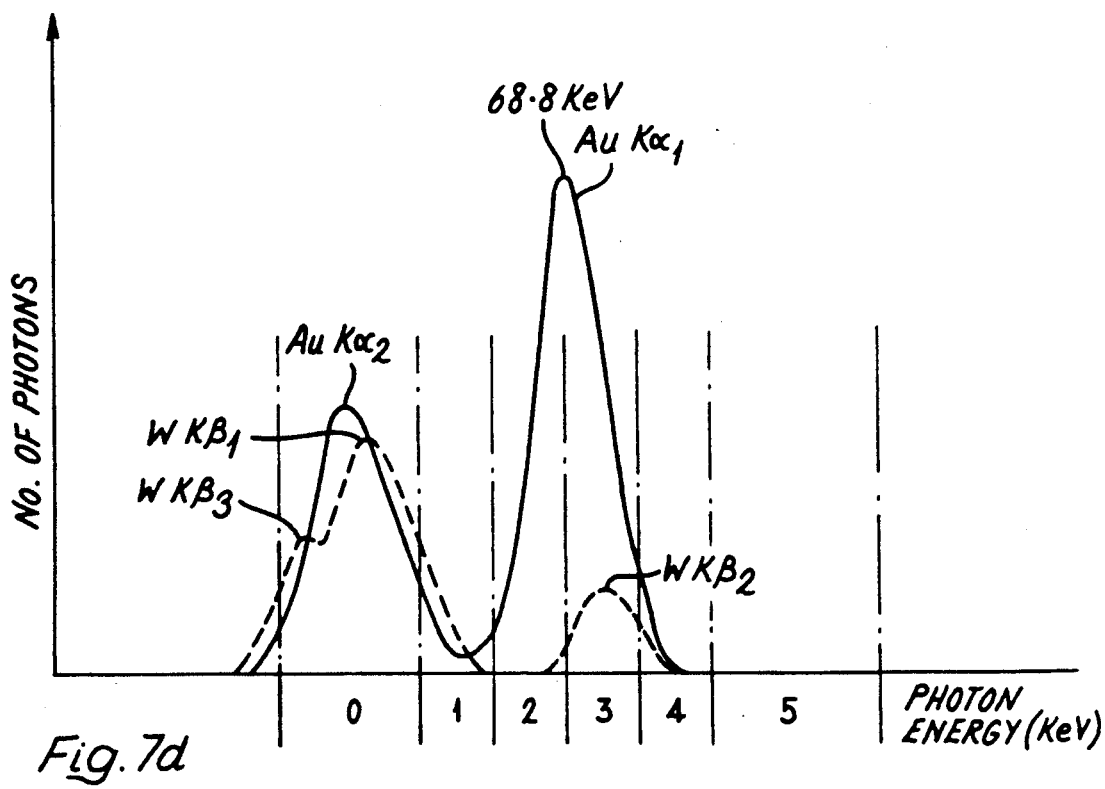

A further application of the selection and allocation of channels according to preferred embodiments of the invention to reduce or eliminate interference from unwanted elements or even to determine the concentration of the same elements is illustrated in FIGS. 7(c) and 7(d). A preferred feature of the invention is the use of an analysis board with six channels, which not only facilitates the determination of certain elements as described below, and is the number required for uranium determination but also simplifies electronic design. FIGS. 7(c) and 7(d), which have been separated for clarity, illustrate the simultaneous detection of interference from mercury and tungsten in analysis for gold.

As shown in FIG. 7(c) the mercury $K\alpha_2$ peak overlaps the gold $K\alpha_1$ peak. The presence of mercury is detected via its $K\alpha_1$ peak in channel 5. This enables the gold result to be questioned or corrected.

In most gold mining areas, the ratio of mercury to gold is very low, and in practice mercury in ore samples is not expected to present a problem. In processed material, however, the mercury may be concentrated relative to the gold. The $K\alpha_2$ peak of thallium overlaps the mercury $K\alpha_1$ peak and can give a false mercury indication. In practice, the occurrence of thallium is rare, and the indication of possible interference is fail-safe.

FIG. 7(d) illustrates the application of this technique to tungsten, the $K\beta$ peaks of which occur at virtually the same energy as the gold peaks but are differently proportioned as regards amplitude. The tungsten $K\beta_2$ peak occurs at a slightly higher energy than the gold $K\alpha_1$ peak, and most of it falls in the signal channels (2+3) with a small amount in channel 4. Part of the tungsten $K\beta_1$ peaks fall in channel 1. The tungsten signal appearing in channel 0 is much greater than the signal appearing in channels (2+3), which contrasts with the gold signal, which is higher in channels (2+3) than in channel 0. Thus the ratio of the total signal in channels (2+3) to the total signal in channel 0 provides an indication of whether or not tungsten is present.

The platinum $K\alpha_1$ peak and the tantalum $K\beta_2$ peaks also appear in channel 0, and can give false indications of tungsten. However, in practice, the occurrence of these elements in ore bodies when gold is the major mineral is rare. The indication of possible interference is fail-safe.

FIG. 10 is a schematic block diagram showing the method and apparatus according to the invention in use. The apparatus consists essentially of a source of high energy X-rays (photons) 201 arranged to bombard a sample in a cylindrical container 202 as described above and below through a collimator 203. Interposed between the X-ray source and the sample 202 is a metallic tin filter 204. The fluorescence photons emitted at right angles to the bombarding rays pass through an iridium filter 205 before collimation to a detector 206 comprising a regular array of germanium detector elements with axes parallel to the incident radiation, each with its own pre-amplification and signal conditioning circuitry.

In FIG. 10, 209 represents a check source, consisting for example of a piece of gold foil in a sample container which is interposed between every, say 4 or 5 ore samples during readings.

The sample container 202 is preferably a cylindrical thin walled container of plastic material such as acetal plastic. A thin container is necessary so that counts due to the sample container are very much less than the counts due to the sample. We have found that generally a diameter in the range of 10–30 mm gives satisfactory results depending on the considerations set forth below, while a wall thickness of 0.35 to 0.5 mm typically about 0.4 mm provides sufficient rigidity, can be made reproducibly, and complies with the above requirement.

The diameter of the sample container can be varied to suit the application and ore bodies. For inhomogenous ore bodies, when sampling error is high, it is desirable to maximise the mass of sample irradiated, and an internal diameter of typically about 18.7 mm is a good compromise between the conflicting requirements of sensitivity and sampling error.

However, the smaller the diameter of the sample container, the higher the sensitivity will be, as there will be less attenuation or absorption of the signal, and less multiple scattering. However, if the sample container is made too small, the effect of counts from its wall will become more noticeable, and also the power of the X-ray generator will have to be greatly increased to provide the high count rate necessary for minimisation of errors due to counting statistics. The sample size will be smaller, and may cause sampling errors. However, for the homogeneous ore bodies, as occur in several parts of the world, the sampling error is low, and a good compromise is a tube having an internal diameter of about 12.7 mm.

The invention is not, however, limited to the use of cylindrical containers with the above dimensions. It is also possible to use differently shaped sample containers with, for example, rectangular cross sections in which the long axis of the rectangular cross section is angled at about 45° to both the exciting beam and the detected beam, so that the desired scattering angle, as described above, is still in the order of 90°.

A further precaution by which inaccuracies due to non-uniform particle size or packing in the sample can be reduced is to shift the sample container, for example along its longitudinal axis, and to measure the scattered radiation in two or more positions of the containers; alternatively the zone of the sample scanned (with the preferred containers of the dimensions mentioned above this is generally about 7 cm long) may be moved along the sample.

The apparatus shown schematically is FIG. 10 employs an automatic sample changer to achieve a continuous throughput of, for example, one sample per 100 seconds. Such rapid throughput is as described above essential in mining applications where continuous analysis of a succession of samples must continue at all times.

It is within the scope of the invention to irradiate the sample with a second beam of exciting X-radiation from a source diametrically opposite to the first source. This technique reduces the gradient of the exciting photons throughout the thickness of the irradiated sample and may also be applied to the use of other types of irradiation source such as special X-ray tubes and radioisotopes; the use of radiootopes source is not however within the scope of the present invention.

I claim:

1. A method for analyzing a sample of ore for at least one heavy metal, said method comprising the steps of:
   exciting the ore with high energy x-rays to produce a fluorescence emission spectrum, and
   measuring the intensity of the K-emission bands of the metal or metals in the spectrum,
   said method further including:
   (a) producing X-rays by using an X-ray tube as a source,
   (b) eliminating most of a high energy bremsstrahlung peak by interposing a metallic filter between the source and the sample to give high energy bremsstrahlung radiation of 100–130 keV incident upon the sample, and
   (c) counting and comparing the number of fluorescence photons emitted in each of a plurality of energy bands, the width and energy of the bands being chosen in relation to K-emission peaks of the at least one heavy metal in the sample, and
   wherein photons are counted in each of two background energy bands lying to either side of a $K\alpha_1$ peak and in each of two signal energy bands lying between the background bands to either side of a peak maximum, total counts of photons in the background and in the signal bands being compared, the two background bands being substantially equal in energy width and the two signal bands being substantially equal in energy width.

2. The method of claim 1, including using tungsten as an anode material of the x-ray tube.

3. The method of claim 1, wherein the ore is powdered gold ore having a gold content of below 10,000 parts per million.

4. The method of claim 2, wherein a gold content in 90% of the ore samples analyzed is up to 10 parts per million.

5. The method of claim 1, 2 or 3, wherein the ore contains and is analyzed for gold and uranium.

6. The method of any of claims 1–4, wherein the filter is tin metal.

7. The method of any of claims 1–4, wherein passing the fluorescence photons emitted by the sample through a heavy metal filter reduces the bremsstrahlung energy peak and thereby enhances a relative number of counts in the K-bands of the at least one heavy metal under analysis.

8. The method of claim 7 in which the filter is of iridium of platinum and the ore contains gold.

9. The method of claim 7 wherein the filter is of osmium and the ore contains platinum.

10. The method of any of claims 1–4, wherein the emitted photons are counted by at least one detector of high purity germanium.

11. The method of claim 10 in which the detector is a disc of active thickness 2–4 mm.

12. The method of any of claims 1–4, wherein the fluorescence spectrum is analyzed at a scattering angle of 80°–100°.

13. A method according to claim 1, wherein said eliminating step includes using a tin metallic filter.

14. The method of claim 1, wherein the ore is analyzed for gold, and wherein the K-emission peak is a gold $K\alpha_1$ peak.

15. The method of claim 1 wherein a sample of ore containing at least one of mercury and tungsten is analyzed for gold, the method further including counting the photons in each of six adjacent energy bands embracing respectively:
(1) a gold $K\alpha_2$ peak on both sides of a maximum,
(2) a trough between the gold $K\alpha_2$ peak and a gold $K\alpha_1$ peak,
(3) a slope of the gold $K\alpha_1$ peak on the low energy side of its maximum,
(4) a slope of the gold $K\alpha_1$ peak on the high-energy side of its maximum,
(5) a trough between the gold $K\alpha_1$ peak and a mercury $K\alpha_1$ peak, and
(6) the mercury $K\alpha_1$ peak on both sides of its maximum.

16. The method of claim 1 for analyzing gold in an ore, the method further comprising:
(a) producing the X-rays by an X-ray tube with one of a plutonium or uranium anode and a secondary target,
(b) exciting the ore sample with characteristic K X-rays of the material of the anode or secondary target, and
(c) passing the fluorescence photons emitted by the same through an iridium filter.

17. A method for analyzing a sample of ore for at least one heavy metal, said method comprising the steps of:
exciting the ore with high energy x-rays to produce a fluorescence emission spectrum, and
measuring the intensity of the K-emission bands of the metal or metals in the spectrum,
said method further including:
(a) producing X-rays by using an X-ray tube as a source,
(b) eliminating most of a high energy bremsstrahlung peak by interposing a metallic filter between the source and the sample to give high energy bremsstrahlung radiation of 100–130 keV incident upon the sample, and
(c) counting and comparing the number of fluorescence photons emitted in each of a plurality of energy bands, the width and energy of the bands being chosen in relation to K-emission peaks of the at least one heavy metal in the sample,
wherein a sample of ore containing thorium is analyzed for uranium and optionally also for gold, the method further including counting the photons in each of six adjacent energy bands embracing respectively:
(1) a thorium $K\beta_2$ peak,
(2) a region immediately above the band of the thorium $K\beta_2$ peak,
(3) an uranium $K\beta_1$ peak,
(4) an uranium $K\beta_3$ peak,
(5) a trough between a uranium $K\beta_2$ peak and a $K\beta_{(1+3)}$ peak, and
(6) the uranium $K\beta_2$ peak.

18. A method of analyzing a sample of ore, said method comprising the steps of:
(a) exciting the sample with high-energy bremsstrahlung X-rays having maximum energy at about 115 keV and produced by an X-ray tube with a tungsten anode and filtered through a metallic tin filter,
(b) passing an X-ray fluorescence spectrum emitted by the sample at right angles to the exciting X-rays through a metallic iridium or platinum filter,
(c) detecting fluorescence photons by a germanium detector, and
(d) measuring intensity of K-emission bands of gold content of the sample.

19. Apparatus for analyzing a heavy metal content of an ore sample, comprising:
(a) a source of high-energy X-rays,
(b) means to hold the sample in a path of the X-rays,
(c) detector means to count fluorescence photons emitted by the sample,
(d) means to compare counts of emitted photons in selected energy bands,
wherein the X-ray source is a tube and a metallic tin filter is interposed between the source and the sample which eliminates part of a high-energy bremsstrahlung peak whereby high energy bremsstrahlung radiation of 100–300 keV is incident on the sample.

20. The apparatus of claim 29 in which an anode is of tungsten.

21. The apparatus of claim 19 or 20 further comprising a heavy metal filter interposed between the sample and the detector means.

22. The apparatus of claim 19 or 20, wherein the detector means is at least one body of high purity germanium.

23. The apparatus of claim 22, wherein the detector means comprises a plurality of high purity germanium discs each 2–4 mm thick.

24. The apparatus of claim 19 or 20, wherein the fluorescence spectrum is viewed at a scattering angle in the range from 80°–100° to the exciting radiation.

25. The apparatus of claim 19 wherein the X-ray source is a tube with one of a plutonium or uranium anode and secondary target, and an iridium filter is interposed between the sample and the detecting means.

26. An apparatus for analyzing at least one of gold and uranium content of a sample of ore by X-ray fluorescence, comprising:
an X-ray tube with a tungsten anode,
a metallic tin filter,
means to hold and retain a sample of ore in a path of the X-rays emitted from the tube and passed through the filter,
an X-ray detector and means to detect the emission of photons of various energies from the sample, wherein one of a metallic platinum and an iridium filter is interposed between the sample and the detectors, and germanium detectors are used.

27. A method according to claim 1 or 14, wherein said method further includes passing fluorescence photons emitted by the sample through a metallic osmium filter before counting them.

* * * * *

UNITED STATES PATENT AND TRADEMARK OFFICE
CERTIFICATE OF CORRECTION

PATENT NO. : 5,020,084

DATED : May 28, 1991

INVENTOR(S) : ROBERTSON

It is certified that error appears in the above-identified patent and that said Letters Patent is hereby corrected as shown below:

Col. 2, line 2, correct "$\delta$-rays" to -- $\gamma$-rays --.

Col. 16, line 56 correct "iridium of platinum" to -- iridium or platinum --

Note: In printed patent copies, Columns 17 and 18 incorrectly precede Columns 15 and 16

Signed and Sealed this

Twenty-seventh Day of April, 1993

Attest:

MICHAEL K. KIRK

Attesting Officer

Acting Commissioner of Patents and Trademarks